United States Patent [19]

Piljac et al.

[11] Patent Number: 5,455,232

[45] Date of Patent: Oct. 3, 1995

[54] PHARMACEUTICAL PREPARATION BASED ON RHAMNOLIPID

[76] Inventors: Goran Piljac, Centar za Biomedicinska Istrazivanja Salata 2, 41000 Zagreb, Yugoslavia; Visnja Piljac, 2323 Shasta Dr., Apt. 76, Davis, Calif. 95616

[21] Appl. No.: 224,070

[22] Filed: Apr. 7, 1994

Related U.S. Application Data

[63] Continuation of Ser. No. 866,691, Apr. 10, 1992, abandoned.

[30] Foreign Application Priority Data

Feb. 4, 1992 [BE] Belgium ................. 9200115

[51] Int. Cl.$^6$ ............... A61K 31/715; A61K 31/70
[52] U.S. Cl. ............... 514/25; 536/4.1; 536/18.2; 514/844; 514/845; 514/846; 514/847; 514/848; 514/858; 514/859; 514/860; 514/861; 514/862; 514/863; 514/864; 514/865; 424/450
[58] Field of Search ............... 424/450; 536/4.1, 536/18.2; 514/25, 844, 845, 846, 847, 848, 858, 859, 860, 861, 862, 863, 864, 865

[56] References Cited

U.S. PATENT DOCUMENTS

| | | | |
|---|---|---|---|
| 3,886,272 | 5/1975 | Parkhurst et al. | 536/5 |
| 3,984,393 | 10/1976 | Magerlein | 536/13.3 |
| 4,317,816 | 3/1982 | Arichi et al. | 514/26 |
| 4,339,442 | 7/1982 | Takemoto et al. | 514/26 |
| 4,371,524 | 2/1983 | Shinohara et al. | 514/33 |
| 4,524,067 | 6/1985 | Arichi et al. | 514/33 |
| 4,554,349 | 11/1985 | Ponpipom et al. | 536/4.1 |
| 4,571,407 | 2/1986 | Chatterjee et al. | 514/464 |
| 4,683,222 | 7/1987 | Stadler et al. | 514/42 |
| 4,753,929 | 6/1988 | Matsumotoj et al. | 536/8 |
| 4,814,272 | 3/1989 | Wagner et al. | 536/18.2 |
| 4,902,512 | 2/1990 | Ishigami et al. | 424/450 |
| 5,043,323 | 8/1991 | Bombardelli et al. | 536/8 |
| 5,057,540 | 10/1991 | Kensil et al. | 536/6.3 |
| 5,071,836 | 12/1991 | Kolar et al. | 530/328 |
| 5,095,123 | 3/1992 | Sabesan | 536/117 |
| 5,128,262 | 7/1992 | Lindoerfer et al. | 536/18.2 |
| 5,175,277 | 12/1992 | Rakitsky et al. | 536/123 |

FOREIGN PATENT DOCUMENTS

WO90/11069 4/1990 WIPO.

OTHER PUBLICATIONS

Patent Abstracts of Japan, vol. 13, No. 61 (C–567) (3409) & JP–A–63 253025.

S. Lang et al., "Antimicrobial Effects of Biosurfactants" (Fat Sci. Technol., vol. 91, Nr. 9, 1989). pp. 363–366.

(List continued on next page.)

*Primary Examiner*—Ronald W. Griffin
*Attorney, Agent, or Firm*—Webb Ziesenheim Bruening Logsdon Orkin & Hanson

[57] ABSTRACT

The invention relates to a pharmaceutical preparation comprising as an active ingredient at least one rhamnolipid or a pharmaceutically acceptable salt thereof, and a carrier and/or diluent, preferably comprising a rhamnolipid of the general formula:

$$CH_3 \begin{array}{c} \\ \diagup \\ O \end{array} \begin{array}{c} O-CH-CH_2-C-O-R_2 \\ | \quad \quad \quad \| \\ R_3 \quad \quad \quad O \end{array}$$
$$HO \diagdown HO \diagup R_1$$

wherein
 $R_1$=H, alpha-L-rhamnopyranosyl;

$$R_2 = H, -CH-CH_2-COOH;$$
$$\quad\quad\quad | \\ \quad\quad\quad R_4$$

$R_3$=($C_5$–$C_{20}$)-saturated, -mono- of poly-unsaturated alkyl;
 $R_4$=($C_5$–$C_{20}$)-saturated, -mono- of poly-unsaturated alkyl.

24 Claims, No Drawings

OTHER PUBLICATIONS

S. Itoh et al., "Rhamnolipids produced by Pseudomonas Aeruginosa grown on n–Paraffin" (The Journal of Antibiotics, vol. 24, Nr. 12, 1971). pp. 855–859.

T. R. Shryock et al., "Effect of Pseudomonas aeruginosa Rhamnolipid on Human Neutrophil Migration" (Current Microbiology, vol. 10, Nr. 6, 1984). pp. 323–328.

Database WPIL, Week 8544, Derwent Publications Ltd., London, GB, AN 85-272338 & JP-A-60 183032.

Patent Abstracts of Japan, vol. 12, No. 306 (C-522)(3153) & JP-A-63 77535.

T. Hirayama et al., "Novel Methyl Rhamnolipids from Pseudomonas Aeruginosa" (FEBS Letters, vol. 139, Nr. 1, Mar. 1982), pp. 81–85.

PHARMACEUTICAL PREPARATION BASED ON RHAMNOLIPID

This is a continuation of application Ser. No. 07/866,691 filed on Apr. 10, 1992, now abandoned.

The present invention relates to a pharmaceutical preparation comprising as an active ingredient at least one rhamnolipid. In particular, the present invention relates to such a pharmaceutical preparation for treatment of dermatological diseases, viral infections, and for cosmetic purposes.

Among bio-surfactants are glycolipids. Due to different combinations of carbohydrates and lipids, together with structural different bonds and different ionic states, there are variety of glycolipids having mutually a strongly different hydrophilic/lipophilic balance. It is known that various strains of Pseudomonas, such as *Pseudomonas aaeruginosa, Pseudomonas fluorescens, Pseudomonas putida, Pseudomonas oleovorans* are capable of extra cellular secretion of rhamnolipids, when growing on soluble and insoluble carbon sources.

The present invention relates to pharmaceutical preparations comprising these rhamnolipids. Based on an extensive research, it has been found that these rhamnolipid based pharmaceutical preparations exhibit a curing action on dermatological diseases, such as *Acnae vulgaris, Pytiriasis versicolor,* Erythrasma, *Piedra alba, Dermatitis allergica contactu, Neurodermitis circumscripta multilocularis, Neurodermitis diffusa, Neurodermitis erythrodermica, Neurodermitis circumscripta chronica unilocularis, Neurodermitis verrucosa, Neurodermitis infantum, Prurigo chronica,* Rosacea, *Dermatitis rosacei formis steroidica, Psoriasis vulgaris, Lichen ruber planus, Strophulus infantum, Urticaria allergica, Dermatitis nummularis eczematoides, Erythema exsudativum multiforme, Epydermolysis bullosa hereditaria dystrophica recessiva, Dermatitis seborrhoica, Erythema nodosum, Pemphygus Vulgaris, Dermatitis herpetiformis Duhring, Lupus erythematosus systemicus,* Herpes simplex infections, Papilloma virus infections, *Ichtyosis vulgaris, Erythrodermia ichtyosiformis, Keratodermitis palmoplantaris, Epidermolysis bullosa hereditaria simplex* and the like.

Preferably, the rhamnolipid is a rhamnolipid of the general formula $$H_3C-\text{(sugar)}-O-\text{(sugar)}-O-CH-CH_2-C(=O)-O-R_2$$
with substituents HO, HO, $R_1$, $R_3$ Very active rhamnolipids are obtained when the rhamnolipid is a di-rhamnolipid.

When the substituent $R_2$ is hydrogen, the rhamnolipid comprises only one lipid group. When the substituent $R_2$ is formed by the group $$CH-CH_2-COOH,$$
$$R_4$$

the rhamnolipid molecule comprises two lipid units mutually connected by an ester bond.

The substituents $R_3$ and $R_4$ may be selected from straight or branched $(C_5-C_{20})$-saturated mono or polyunsaturated alkyl groups. Preferred are unbranched, saturated alkyl groups having the general formula $(CH_2)_x-CH_3$, wherein $x=4-20$. More preferably $x=4$ or $6$ for the alkyl groups.

A very active pharmaceutical preparation is obtained when it comprises the rhamnolipid is (alpha-L-rhamnopyranosyl-(1,2) alpha-L-rhamnopyranosyl)-3-hydroxydecoanoyl-3-hydroxydecanoic acid.

Based on a non-limitative example, the isolation of rhamnolipid and the use in a pharmaceutical preparation according to the present invention will be described. Herein the following methods will be used.

1. Isolation and Characterization

From oil well drilling mud bacterial strains have been isolated, which strains can synthesize rhamnolipids both on a soluble carbon source (glucose) as on a insoluble carbon source (glycerol, gas oil). These isolated bacterial strains have been characterized as Pseudomonas strains (BBL Minitek, Numerical Determination and Identification System, Becton, Dichinson and Company).

2. Concentration and Purification

The rhamnolipids present in the medium due to extra cellular secretion have been concentrated and purified using different procedures.

a) Acid Precipitation

The pH of the supernatant was adjusted to pH 1.5–2.0 using hydrochloric acid, then it was evaporated to 1/10 of the initial volume and left over the night at 4° C. Pellet (0.5–2.0 g/l) was centrifuged at 17.300×g for 30 minutes at 4° C. and subsequently extracted using $CH_2Cl_2$, filtrated, evaporated, resuspended in water and precipitated again.

b) Foam Fractionation

Compressed air was introduced into the supernatant and foam formed was passed into a separate container, or was introduced in acidified water (pH 1.5–2.0).

c) Chromatography

Supernatant was applied on a preparative column (Amberlit XAD-8 or XAD-2 resin, Rohm & Haas). The column was equilibrated using water, and after absorption rinsed with water. The active compounds were eluted using a lower alkyl alcohol, such as ethanol and methanol. The solvent used was evaporated under vacuum and the concentrate was acidified and precipitated as described above.

3. Chemical Detection and Characterization

Thin layer chromatography was performed analytically using silica gel 60F 254 plates (Merck), and performed preparatively using Kemika plates. For an optimal separation the following solvent mixtures may be used $CHCl_3$—MeOH—acetic acid-water (25:15:4:2; 12:15:4:2; 25:25:4:2) $CHCl_3$—MeOH—acetic acid (80:15:5) Hexane-isopropyl ether-acetic acid (15:10:1) $CHCl_3$—MeOH—$NH_4OH$ (25%)-water (65:25:4:2) propanol-$NH_4OH$ (25%) (4:1).

EXAMPLE

*Pseudomonas aeruginosa* was cultured at a temperature of 32° C. The following culture media were very suitable for rhamnolipid production.

a) 5 g glucose, 5 g peptone, 2 g yeast extract, 5 g NaCl, 0,5 g $KH_2PO_4$, 2 g $MgSO_4.H_2O$, 3 g $KNO_3$, 1 ml Gottlib solution and 1 liter water.

b) 20 g glucose, 10 g yeast extract, 20 g $CaCO_3$ and 1 liter water.

Glucose may be replaced by glycerol, whereby a two phase system is formed. As a carbon source glycerol provides a better yield in comparison to glucose, but a more complicated process is required. The change in surface tension of the culture media to 28–31 mN/m was measured using a White's ring tensiometer. A decrease of the surface tension is a good indication of the yield at the end of the fermentation. The rhamnolipid concentration was measured spectrophotometrically using anthrone reagents. After separation of the biomass by centrifugation, the supernatant was chromatographed on silica gel 60 F 254 plates and on Kemika plates.

The presence of glycolipids was proved using the following reagents, alpha naphthol for lipids, diphenylamine for glycolipids, and beta naphthol thymol and anthrone for carbohydrates and oligosaccharides. Using these reagents, it is proved that the compounds are of the glycolipid type. Using alphacyclodextrin, reagent and dye for fatty acids, it is proved that the lipophilic/hydrophilic part of the molecule consists of fatty acid chains having an even number of carbon atoms. Negative results were obtained using reagents for unsaturated lipids. Using alkali $KMnO_4$ and ammoniacal $AgNO_3$, the presence of glycosidic bonds has been proved. Using alkali hydrolysis ester bonds between fatty acids are split, and using acidic hydrolysis, the O-glucosidic bond between a sugar group and the OH group of the lipid part of the molecule is split.

10 Volumina of the supernatant comprising rhamnolipids was passed over an amberlit XAD-8 of XAD-2 column (Rohm & Haas). The column was washed with water. The rhamnolipids were eluted using 100% MeOH. The fractions comprising rhamnolipids were evaporated and subsequently added to pure water.1 N HCl was added to precipitate the rhamnolipids. Precipitated rhamnolipids were centrifuged at 3000 rpm for 10 minutes. The rhamnolipids now precipitated were washed using pure water and subsequently centrifuged at 3000 rpm for 10 minutes. Using 1/10N NaOH the pH of the precipitated lipids were adjusted to 7.2. After lyophilization 10 g of the lyophilized preparation was dissolved in 50 ml propanol and applied to a silica column (Waters HPLC, volume 500 ml) equilibrated with hexane. Using 5 l propanol impurities were eluted. The rhamnolipids were eluted using a solvent mixture comprising propanol-25% $NH_4OH$ (4:1). The active fractions were evaporated and dissolved in water, again precipitated in 1N HCl, centrifuged at 3000 rpm, and the precipitants were adjusted to pH 7.2 using 0.1N NaOH, and lyophilized.

The pure rhamnolipids obtained were used for preparing pharmaceutical preparations according to the invention. These preparations may comprise solutions, ointment, cremes, gels, fluids, powders, pills and the like.

Dependent on the disease to be treated, such as dermatological diseases, the seriousness of the disease, the age of the patient, and the like, pharmaceutical preparations may comprise 0.05 to 10% by weight active rhamnolipid. Preferably, the rhamnolipid concentration is 0.1 to 2.0% by weight, more preferably 0.1 to 1.0% by weight. The under limit is determined by the activity of the present rhamnolipid and the upper limit is predominantly determined economically.

Formulation Example

A ointment base was enriched using 1.0% by weight rhamnolipid. The rhamnolipid was (alpha-L-rhamnopyranosyl-(1,2) alpha-L-rhamnopyranosyl)-3-hydroxydecoanoyl-3-hydroxydecanoic acid, and was identified using i) $^1H$ and $^{13}C$—NMR data; and ii) massaspectrophotometric data.

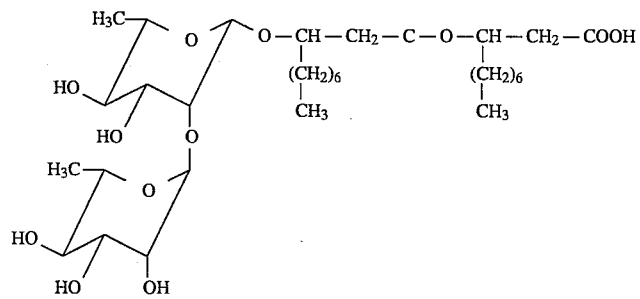

$^{13}C$-NMR (75 MHz; DMSO-d6)

| C | ppm | C | ppm | C | ppm |
|---|---|---|---|---|---|
| 1" | 97,7 | 1 | 173,3 | 1' | 170,6 |
| 2" | 77,3 | 2 | 40,8 | 2' | 40,2 |
| 3" | 70,4a | 3 | 72,2a | 3' | 71,4a |
| 4" | 73,2 | 4 | 33,7 | 4' | 32,5 |
| 5" | 68,9 | 5 | 24,8 | 5' | 24,1 |
| 6" | 17,9 | 6 | } 28,8–29,2 | 6' | } 28,8–29,2 |
| 1''' | 102,2 | 7 | | 7' | |
| 2''' | 70,4a | 8 | 31,4 | 8' | 31,4 |
| 3''' | 70,8a | 9 | 22,2 | 9' | 22,2 |
| 4''' | 72,4 | 10 | 14,0 | 10' | 14,0 |
| 5''' | 68,8 | | | | |
| 6''' | 17,8 | | | | | a: assignments may be reversed $^1H$-NMR (300 MHz, DMSO-d6)

-continued sugar part

| H | ppm | |
|---|---|---|
| 1"; 1'" | 4,8; 4,9 | 2x singlet (2H) |
| 2"; 2'" ↓ 5"; 5'" | 3,20 → 4,10 | multiplet (8H) |
| 6"; 6'" | 1,21 | doublet, J=5,9Hz (6H) | lipid part

| H | ppm | |
|---|---|---|
| 2,2' | 2,43, 2,53 | 2x doublet, J=6,0Hz (4H) |
| 3,3' | { 3,20–4,1 / 5,24 | multiplet (2H) |
| 4,4' | 1,6 | multiplet (4H) |
| 5,5' → 9,9' | 1,3 | multiplet (16H) |
| 10,10' | 0,97 | triplet, J=6,3Hz (6H) | massaspectra m/z: 673 [M + H + Na]$^+$
m/z: 695 [M + H + 2Na]$^+$
m/z: 525 [M − $C_{10}H_{18}O_2$ + 2Na]$^+$ minus terminal lipid
m/z: 379 [M − $C_{10}H_{18}O_2$ − rhamnose + 2Na]$^+$ minus terminal lipid and rhamnose For human patient the following dermatological diseases were treated using the preparation according to the formulation example: *Psoriasis pustulosa, Neurodermitis chronica multilocularis, Lichen ruber planus* and *Acne papulopustulosa*. The treatment of affected skin surfaces for a period of about two weeks resulted in a substantially total disappearance of the features of the dermatological diseases.

We claim:

1. A method for treating dermatological conditions comprising topically administering, to a patient requiring treatment of a dermatological condition, a pharmaceutical preparation comprising an amount of a rhamnolipid or a pharmaceutically acceptable salt thereof effective to treat said dermatological disease, together with at least one pharmaceutically acceptable excipient, wherein said disease is selected from the group consisting of *Dermatitis allergica contactu, Neurodermitis circumscripta multilocularis, Neurodermitis diffusa, Neurodermitis erythrodermica, Neurodermitis circumscripta chronica unilocularis, Neurodermitis verrucosa, Neurodermitis infantum, Prurigo chronica,* Rosacea, *Dermatitis rosacei formis steroidica, Psoriasis vulgaris, Lichen ruber planus, Strophulus infantum, Urticaria allergica, Dermatitis nummularis ezematoides, Epydermolysis bullosa hereditaria dystrophica recessive, Dermatitis seborrhoica, Erythema nodosum, Pemphygus vulgaris, Dermatitis herpetiformis Duhring, Lupus erythematosus systemicus,* Herpes simplex infections, Papilloma virus infections, *Ichtyosis vulgaris, Erythrodermia Ichtyosiformis, Keratodermitis palmoplantaris,* and *Epidermolysis bullosa hereditaria simplex.*

2. The method according to claim 1, wherein said rhamnolipid has the formula:

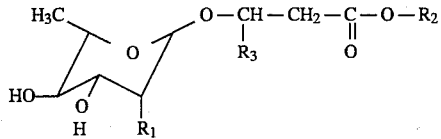

wherein $R_1$=H, alpha-L-rhamnopyransoyl;

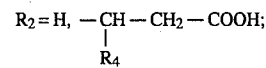

$R_3$=($C_5$–$C_{20}$)-saturated, -mono- or poly-unsaturated alkyl; and $R_4$=($C_5$–$C_{20}$)-saturated, -mono- or poly-unsaturated alkyl.

3. The method according to claim 2, wherein said rhamnolipid has the formula wherein $R_3$=—$(CH_2)_x$—$CH_3$, wherein x=4–20.

4. The method according to claim 2, wherein said rhamnolipid has the formula wherein $R_4$=—$(CH_2)_x$—$CH_3$, wherein x=4–20.

5. The method of claim 2 wherein $R_1$ is alpha-L-rhamnopyranosyl.

6. The method of claim 5 wherein $R_3$ is —$(CH_2)_x$—$CH_3$, wherein x is 4 or 6.

7. The method of claim 5 wherein $R_4$ is —$(CH_2)_x$—$CH_3$, wherein x is 4 or 6.

8. The method of claim 1 wherein said rhamnolipid is (alpha-L-rhamnopyranosyl-(1,2) alpha-L-rhamnopyranosyl)-3-hydroxydecoanoyl-3-hydroxydecanoic acid.

9. The method of claim 1 wherein said rhamnolipid has a concentration between about 0.05 and 10% by weight of said preparation.

10. The method of claim 9 wherein said rhamnolipid has a concentration between about 0.1 and 2.0% by weight of said preparation.

11. The method of claim 10 wherein said rhamnolipid has a concentration between about 0.1 and 1.0% by weight of said preparation.

12. A method for treating a dermatological condition comprising topically administering, to a patient requiring treatment of a dermatological condition selected from the group consisting of *Psoriasis pustulose, Neurodermatitis chronica multilocularis*, and *Lichen ruber planus*, an amount of a rhamnolipid or a pharmaceutically acceptable salt thereof effective to treat said dermatological disease, in combination with at least one pharmaceutically acceptable excipient.

13. The method of claim 12 wherein said rhamnolipid has the formula:

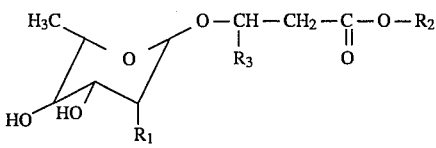

wherein $R_1$=H, alpha-L-rhamnopyranosyl;

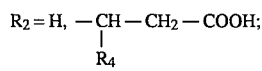

$R_3$=($C_5$–$C_{20}$)-saturated, -mono- or polyunsaturated alkyl; and $R_4$=($C_5$–$C_{20}$)-saturated, -mono- or polyunsaturated alkyl.

14. The method of claim 13 wherein said rhamnolipid has the formula wherein $R_3$=—$(CH_2)_x$—$CH_3$, wherein x=4–20.

15. The method of claim 13 wherein said rhamnolipid has the formula wherein $R_4$=—$(CH_2)_x$—$CH_3$, wherein x=4–20.

16. The method of claim 13 wherein $R_1$ is alpha-L-rhamnopyranosyl.

17. The method of claim 16 wherein $R_3$ is —$(CH_2)_x$—$CH_3$, wherein x is 4 or 6.

18. The method of claim 17 wherein $R_4$ is —$(CH_2)_x$—$CH_3$, wherein x is 4 or 6.

19. The method of claim 13 wherein said rhamnolipid is (alpha-L-rhamnopyranosyl-(1,2) alpha-L-rhamnopyranosyl)-3-hydroxydecoanoyl-3-hydroxydecanoic acid.

20. The method of claim 12 wherein said rhamnolipid has a concentration between about 0.05 and 10% by weight of said preparation.

21. The method of claim 20 wherein said rhamnolipid has a concentration between about 0.1 and 2.0% by weight of said preparation.

22. The method of claim 21 wherein said rhamnolipid has a concentration between about 0.1 and 1.0% by weight of said preparation.

23. A method for treating psoriasis comprising administering to a patient in need thereof a pharmaceutical preparation consisting essentially of a rhamnolipid or pharmaceutically acceptable salt thereof, together with at least one pharmaceutically acceptable excipient, said rhamnolipid having a concentration between about 0.05 and 10% by weight of said preparation.

24. The method of claim 23 wherein said rhamnolipid has the formula:

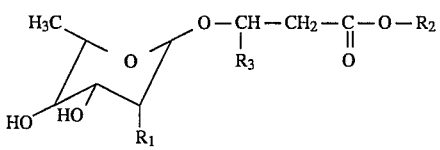

wherein $R_1$=H, alpha-L-rhamnopyranosyl;

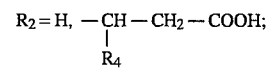

$R_3$=($C_5$–$C_{20}$)-saturated, -mono- or polyunsaturated alkyl; and $R_4$=($C_5$–$C_{20}$)-saturated, -mono- or polyunsaturated alkyl.

* * * * *

UNITED STATES PATENT AND TRADEMARK OFFICE
CERTIFICATE OF CORRECTION

PATENT NO. : 5,455,232           Page 1 of 2
DATED      : October 3, 1995
INVENTOR(S): Goran Piljac and Visnja Piljac It is certified that error appears in the above-indentified patent and that said Letters Patent is hereby corrected as shown below:

Title page, section [56] References Cited, U.S. PATENT DOCUMENTS, "4,753,929  6/1988  Matsumotoj et al. ... 536/8" should read --4,753,929  6/1988  Matsumoto et al. ... 536/8--.

Column 1 Line 13 "variety" should read --varieties--.

Column 2 Line 2 after "rhamnolipid" delete "is".

Column 2 Line 13 "a insoluble" should read --an insoluble--.

Column 2 Line 60 "*aeruginosa*" should read --*aaeruginosa*--.

Column 2 Line 65 "0,5" should read --0.5--.

Column 4 Line 4 "were" should read --was--.

Column 4 Line 30 "A ointment" should read --An ointment--.

Claim 1 Line 44 Column 5 "disease," should read --condition,--.

Claim 1 Line 45 Column 5 "disease" should read --condition--.

UNITED STATES PATENT AND TRADEMARK OFFICE
CERTIFICATE OF CORRECTION

PATENT NO. : 5,455,232
DATED : October 3, 1995
INVENTOR(S) : Goran Piljac and Visnja Piljac It is certified that error appears in the above-indentified patent and that said Letters Patent is hereby corrected as shown below:

Claim 12 Line 10 Column 7 "disease," should read --condition,--.

Claim 18 Line 44 Column 7 "17" should read --16--.

Signed and Sealed this

Ninth Day of April, 1996

Attest:

BRUCE LEHMAN

Attesting Officer

Commissioner of Patents and Trademarks